United States Patent [19]

Buelna

[11] Patent Number: 5,443,449
[45] Date of Patent: Aug. 22, 1995

[54] CHOLANGIOGRAPHY CATHETER

[75] Inventor: Terrance J. Buelna, Rancho Santa Margarita, Calif.

[73] Assignee: Applied Medical Resources Corporation, Laguna Hills, Calif.

[21] Appl. No.: 80,972

[22] Filed: Jun. 22, 1993

Related U.S. Application Data

[63] Continuation of Ser. No. 664,067, Mar. 1, 1991, abandoned.

[51] Int. Cl.⁶ ............................................. A61M 29/00
[52] U.S. Cl. ..................... 604/105; 604/96; 604/264; 606/192
[58] Field of Search .............. 606/191, 192, 194; 604/96-109, 264, 280

[56] References Cited

U.S. PATENT DOCUMENTS

| | | | |
|---|---|---|---|
| 3,397,699 | 8/1968 | Kohl . | |
| 3,568,659 | 3/1971 | Karnegis | 604/105 |
| 4,043,338 | 8/1977 | Homm et al. | 604/105 |
| 4,263,917 | 4/1981 | Moss | 606/192 |
| 4,516,578 | 5/1985 | Shuffield | 604/104 |
| 4,572,186 | 2/1986 | Gould . | |
| 4,699,611 | 10/1987 | Bowden | 606/191 |
| 4,723,549 | 2/1988 | Wholey et al. | 606/194 |
| 4,779,611 | 10/1988 | Grootes | 604/96 |
| 4,861,337 | 8/1989 | George | 604/96 |
| 4,919,651 | 4/1990 | Doane | 604/96 |
| 5,049,131 | 9/1991 | Deuss | 606/194 |
| 5,053,009 | 10/1991 | Herzberg | 604/105 |
| 5,071,429 | 8/1990 | Pinchuk et al. | 604/96 |
| 5,073,166 | 12/1991 | Parks et al. | 604/105 |

FOREIGN PATENT DOCUMENTS 3818279  12/1989  Germany ............... 606/194

Primary Examiner—C. Fred Rosenbaum
Assistant Examiner—Chalin Smith
Attorney, Agent, or Firm—Richard L. Myers

[57] ABSTRACT

An occlusion catheter includes a catheter body and an expansion section disposed at the distal end of the catheter body. This section is operable between a low profile state which facilitates insertion of the catheter into a body conduit, and a high profile state which facilitates occlusion of the body conduit by the catheter. An elastomeric sleeve disposed to be carried outwardly by the expansion section forms a continuous concave surface for occluding the body conduit.

29 Claims, 4 Drawing Sheets

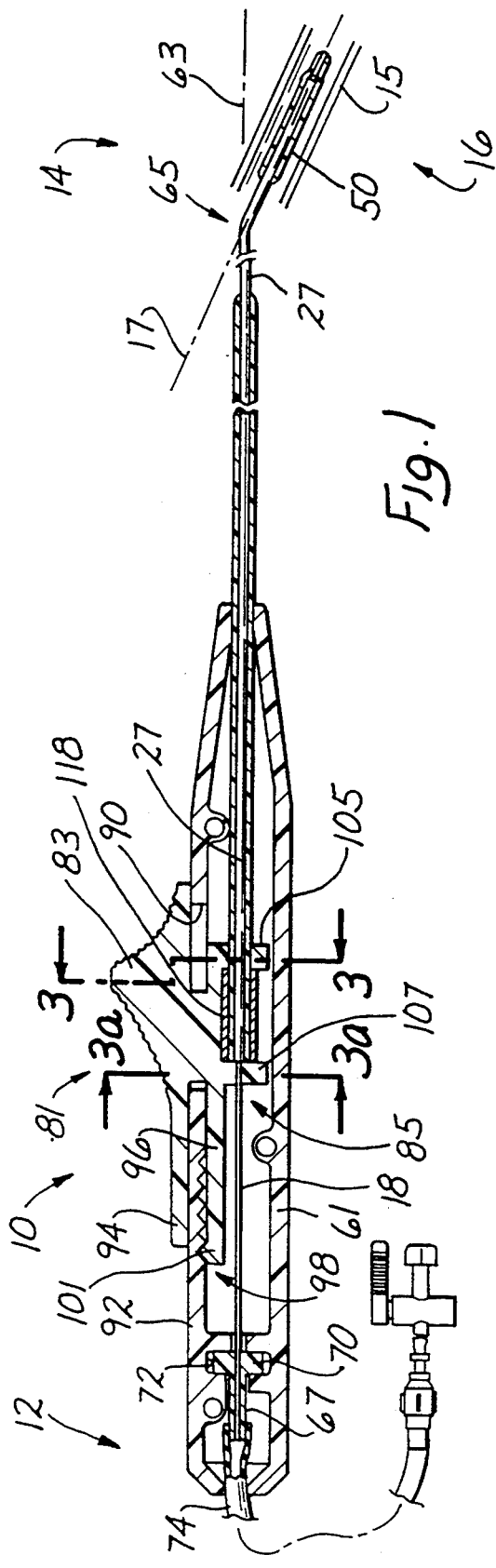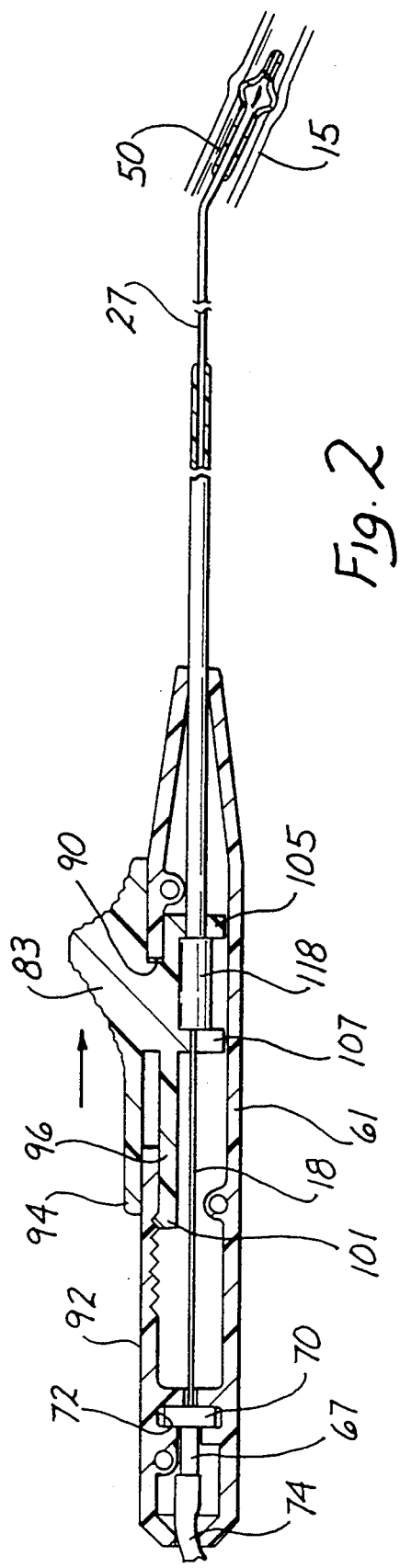

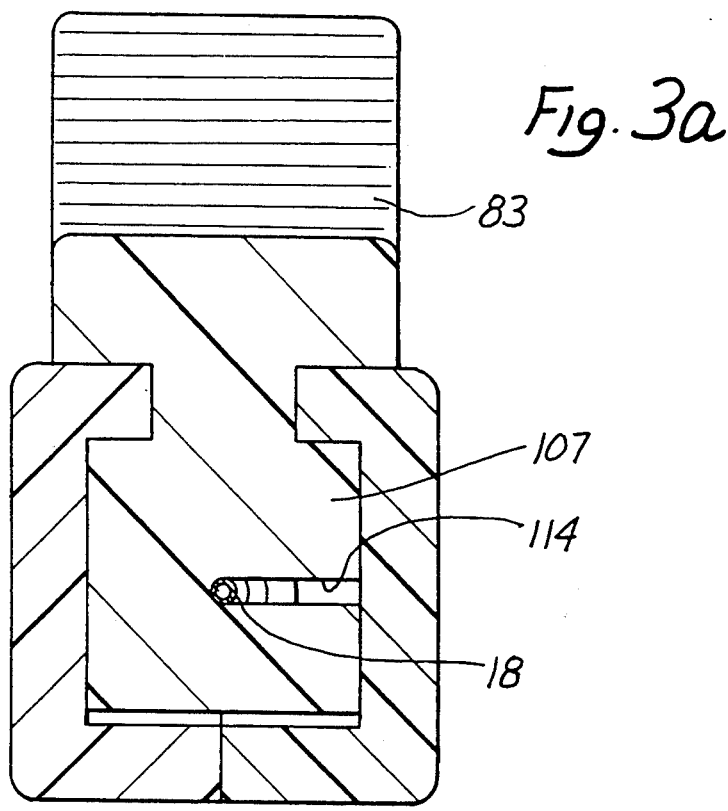
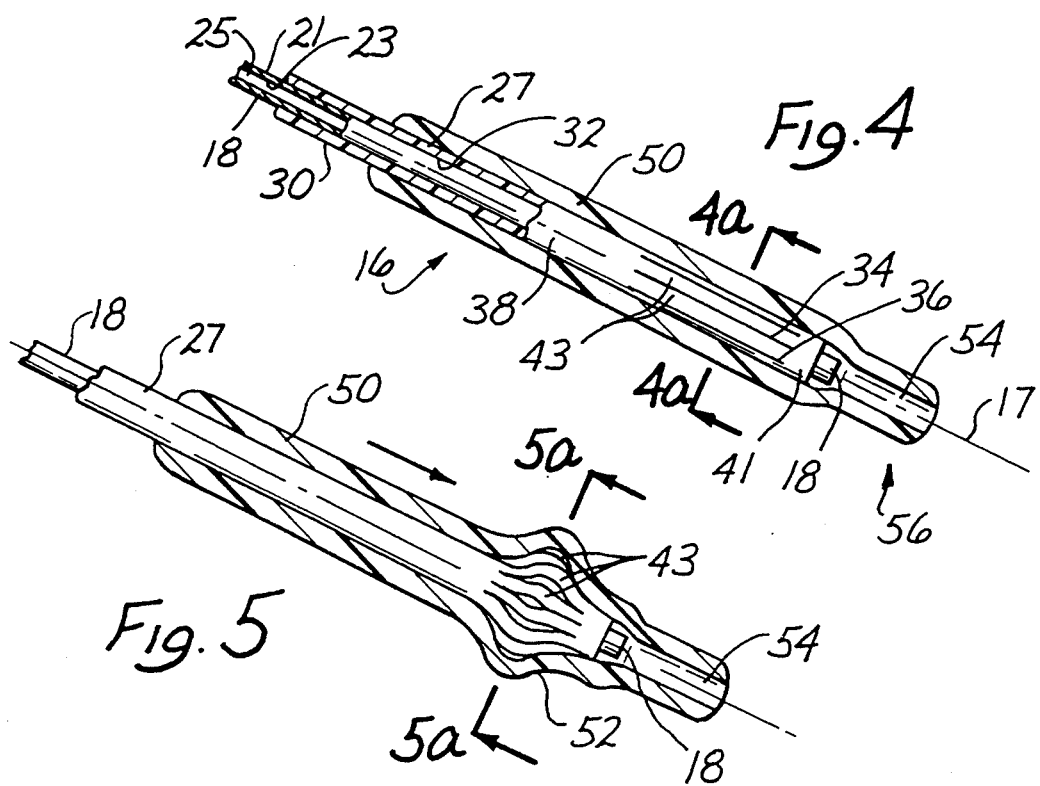

CHOLANGIOGRAPHY CATHETER

This application is a continuation of application Ser. No. 07/664,067, filed Mar. 1, 1991 now abandoned and also entitled "Cholangiography Catheter".

BACKGROUND OF THE INVENTION

Angiography procedures in general require a device for introducing a radiopaque fluid into a body conduit. Radioscopic visualization of this fluid in the conduit provides a picture of the interior shape of the conduit and, more importantly, a view of any obstructions which may be occluding the conduit. This process is particularly important in a procedure which is commonly referred to as cholangiography where the bile ducts are infused with the radiopaque fluid to show obstructions such as gallstones.

Although gallstones are of mixed composition, their most common constituent appears to be cholesterol. Under normal circumstances this cholesterol is prevented from flowing out of the body by a delicate balance of bile salts and phospholipids. However, change in this balance can produce a increase in cholesterol and a decrease in bile salts; this generally leads to formation of the gallstones.

These stones can remain in the gall bladder for many years without causing distress, but sometimes a gallstone slips out of the gall bladder into the biliary tree. If this stone is too large to pass easily through the bile duct, it may cause an obstruction to the flow of bile, an extremely serious problem.

Biliary obstruction due to stones is one of the more common causes of jaundice. Any obstruction of the bile duct causes the bile to back up in the biliary tree eventually making it impossible for the liver cells to secrete bile. Thus the bile builds up and the substances which produce the bile begin to collect in the blood stream. This eventually results in the yellowing which characterizes jaundice.

Since gallstones most commonly form in the gall bladder, it is sometimes desirable to sacrifice the normal function of the gall bladder (to collect and concentrate the bile) in favor of removing this stone-producing organ. In a procedure called cholecystectomy, the cystic duct, which connects the gall bladder to the common bile duct, is ligated and the gall bladder is removed from the body along with any stones in the gall bladder.

In order to fully address the gallstone problem, this procedure requires that the physician also view the system of ducts, commonly referred to as the biliary tree, for any stones which may have already migrated from the gall bladder. A cholangiography catheter is inserted through an incision in the cystic duct. The radiopaque fluid is injected through the catheter into the cystic duct and on to the biliary tree. Of course it is important to maintain this fluid in the ducts long enough to permit the necessary visualization. In order to seal the cystic duct and thereby prevent retrograde flow of the radiopaque fluid, a staple or ligating loop is typically applied between the point of incision and the distal injection port of the catheter.

This initial staple is loosely applied before the catheter is inserted and the catheter is moved through the duct and the loose staple. Then a second staple is applied tightly around the duct and the catheter. It requires a high degree of skill to apply the initial staple tight enough to obstruct the duct but loose enough to permit insertion of the catheter. It takes even more skill to tighten the second staple sufficiently to occlude the duct around the catheter but loose enough to avoid collapsing the catheter prior to injection of the fluid.

A significant need has remained for a device which can inject radiopaque fluid into a body conduit and form a seal within the conduit to prevent retrograde flow of the injectate. A device which cannot only provide such a seal but also anchor the catheter in this position would be of particular advantage.

SUMMARY OF THE INVENTION

These problems are overcome with the present invention which is characterized by an angiography catheter having an elongate catheter body extending from a proximal end to a distal end, and an overlying elastomeric sleeve at the distal end of the catheter. Means is provided beneath the sleeve for expanding the sleeve radially outwardly into sealing and anchoring contact with the interior surface of the body conduit. In a particular embodiment, the angiography catheter includes an inner tube extending axially from the proximal end to the distal end of the catheter. The radiopaque fluid is injectable through this inner tube.

An outer sheath closely overlies this inner tube and extends from a proximal thumb tab to the distal end of the catheter. In proximity to this distal end, the outer tube is provided with axial slits which divide the tube circumferentially into a plurality of fingers. The outer tube is bonded to the inner tube distally of these fingers.

An elastomeric sleeve is positioned over the fingers and moved radially outwardly when the outer tube is slid distally along the inner tube. This movement is created by the user's operation of the thumb tab. As the fingers expand radially outwardly, they press the elastomeric sleeve against the inner surface of the body conduit forming a seal within the conduit.

Preferably these fingers are constructed to form a seal having a small area of contact with the body conduit. This construction insures that the force applied by the fingers creates a relatively high pressure against the wall of the conduit. This also tends to anchor the catheter for injection of the infusate. With the fingers disposed in the expanded state, the elastomeric sleeve forms a seal and anchors the catheter to prevent retrograde flow of the radiopaque fluid.

In one aspect of the invention an infusion catheter is provided with a proximal end and a distal end, and is adapted for insertion into a body conduit and operable to occlude the body conduit. The catheter includes a catheter body disposed along a longitudinal axis and having an outer surface. Means is disposed in proximity to the distal end of the catheter and has a low profile state for facilitating insertion into the body cavity and a high profile state for facilitating occlusion of the body conduit. An elastomeric sleeve is disposed in circumferential relationship with the facilitating means and forms a continuous surface which extends increasingly radially with progressive positions along the axis of the catheter.

In a further aspect of the invention, an infusion device is provided for directing an infusate into a body conduit. The device includes a catheter body having walls defining a central conduit extending along the longitudinal axis, and an exit port extending from the central conduit through the walls of the catheter body. An elastomeric sleeve is disposed proximally of the exit port with a first end of the sleeve attached to proximal portions of the catheter body and a second end of the sleeve attached to distal portions of the catheter body. Means is disposed between the proximal portions and the distal portions for expanding the sleeve radially outwardly to form a circular seal with the body conduit. Means is also provided for injecting the infusate through the catheter body and the exit port into the body.

In an associated method for injecting a fluid into a body conduit, a catheter is provided having a longitudinal configuration and walls defining a lumen extending from the proximal end of the catheter to the distal end of the catheter. The catheter includes and occlusion device at the distal end which is operable to expand from a low profile state to a high profile state. The method provides for inserting into the body cavity the distal end of the catheter including the occlusion device in its low profile state. Then, the occlusion device can be operated to expand to the high profile state wherein it contacts the body conduit interiorly to form the occluding seal. Finally, the fluid can be injected through the catheter into the body cavity with the seal inhibiting retrograde flow of the fluid.

These and other features and advantages of the invention will be more apparent with a discussion of preferred embodiments and reference to the associated drawings.

DESCRIPTION OF THE DRAWINGS

FIG. 1 is a side elevation view in axial cross-section of a preferred embodiment of the catheter of the present invention with its distal tip operatively disposed in a low profile state in a conduit;

FIG. 2 is an axial cross-section view similar to FIG. 1 and illustrating the distal tip operatively disposed in an expanded state in the conduit;

FIG. 3a is a radial cross-section view taken along lines 3a—3a of FIG. 1;

FIG. 4 is an enlarged axial cross-section view illustrating the distal tip in its collapsed, low-profile state;

FIG. 5 is an enlarged axial cross-section view of the distal tip illustrated in its expanded, occlusion state;

DESCRIPTION OF PREFERRED EMBODIMENTS

Figure 3:
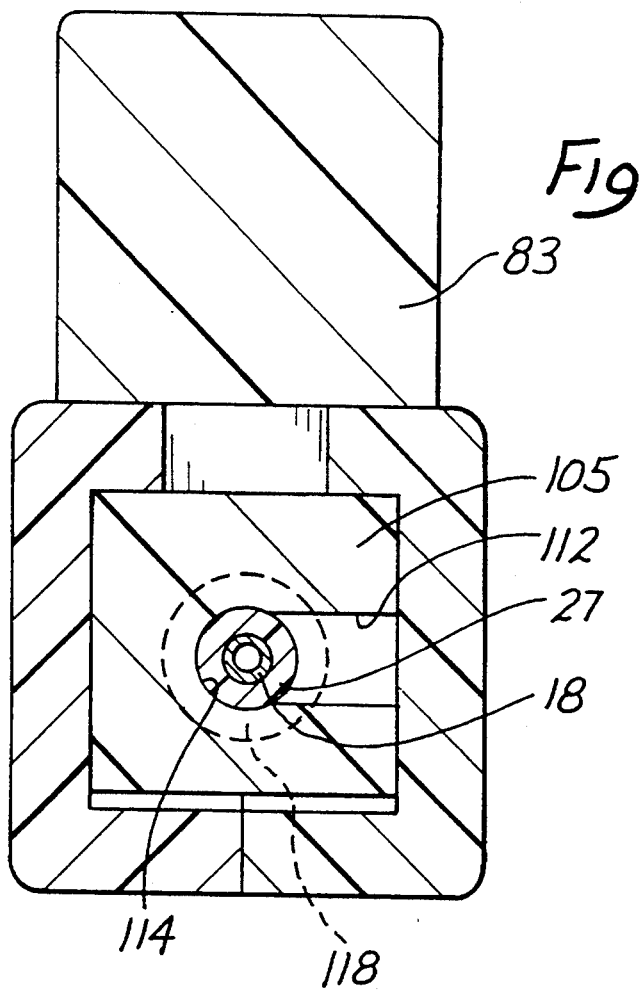
FIG. 3 is a cross-section view taken along lines 3—3 of FIG. 1.

An occlusion catheter is illustrated in FIG. 1 and designated generally by the reference numeral 10. The catheter 10 has a longitudinal configuration and extends from a proximal end 12 to a distal end 14. The catheter 10 is generally representative of any longitudinal device having near its distal end 14 a section which is expandable from a low profile state to a high profile state. The low profile state facilitates insertion of the distal end 14 into a conduit while the high profile state facilitates formation of an occlusive seal with the walls of the conduit.

This concept is particularly advantageous with respect to surgical devices, such as the catheter 10, wherein the distal end 14 can be inserted through an incision into a body orifice, passage or other conduit 15, and expanded to occlude that conduit.

Figure 4A:
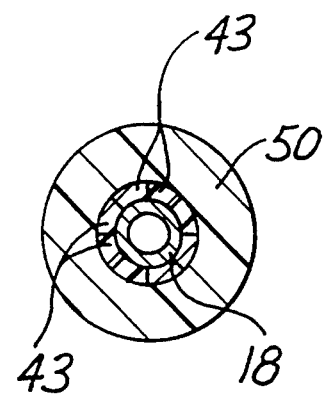
FIG. 4a is a radial cross-section view taken along lines 4a—4a of FIG. 4.

Thus, as best illustrated in the enlarged view of FIG. 4, the catheter 10 includes an expandable tip section 16 disposed at the distal end 14 of the catheter 10. The tip section 16 is defined generally with respect to a longitudinal axis 17, and includes a central element having the configuration of a rod or tube 18. In the case of the tube 18, the central element has an outer surface 21, and an inner surface 23 which defines a central lumen 25. In a preferred embodiment the tube 18 has a rigid configuration and is formed from stainless steel.

An outer tube 27 is disposed in overlying and circumferential relationship with respect to the inner tube 18. The tube 27 has an outer surface 30 and an inner surface 32 which is slidable relative to the outer surface 21 of the tube 18. That is to say, if the central tube 18 is stationary, the outer tube 27 is movable outside the inner tube 18; or, in the alternative, if the outer tube 27 is stationary, the inner tube 18 is movable inside the outer tube 27.

It is of particular importance to the present invention that portions of the outer tube 27 define at least two opposing slots or slits 34, 36 which extend entirely through the outer tube 27 from the outer surface 30 to the inner surface 32. These slits 34, 36 are preferably straight and aligned with at least a component in the longitudinal direction. Thus the slits 34, 36 can be transverse (but not perpendicular) to the axis 17, or parallel to the axis 17 as in the illustrated embodiment.

In the longitudinal direction, the slits 34, 36 extend from a proximal section 38 of the outer tube 27 to a distal section 41 of the outer tube 27. The slits 34, 36 are representative of a plurality of such slits that define at least two fingers 43 which are disposed radially with respect to each other around the outer tube 27 and extend between the proximal section 38 and a distal section 41 of the tube 27. In a preferred embodiment, there are seven fingers 43 which are individually disposed to extend parallel to the axis 17 and collectively disposed at equal angles of about 51° around the circumference of the outer tube 27.

It is this configuration of fingers 43 which provides the tip section 16 with its characteristics for changing between the low profile state and the high profile state.

In this embodiment, the relatively slidable characteristics of the tubes 18, 27 are preserved along the entire catheter 10 except at a location which is distal of the fingers 43. For example, in a preferred embodiment, the outer tube 27 is fixed to the inner tube 18 at the distal section 41. But proximally of the distal section 41, the tubes 18, 27 are free to slide relative to each other. With this structural configuration, relative movement of the tubes 18, 27 proximally of the distal section 41 results in the radial expansion and collapse of the fingers 43.

Figure 5A:
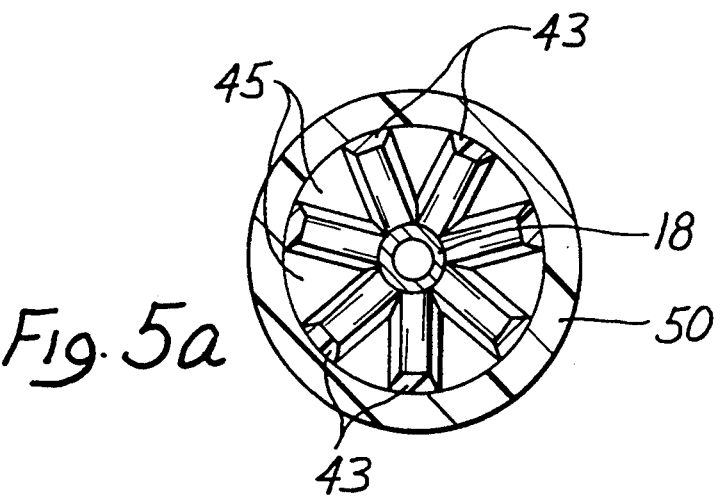
FIG. 5a is a radial cross-section view taken along lines 5a-5a of FIG. 5.

In this particular case, the outer tube 27 functions as a catheter body and the inner rod or tube 18 engages the catheter body distally of the fingers 43 to expand the fingers 43 radially outwardly into circumferential proximity with the body conduit 15. In the low profile state, the fingers 43 are radially collapsed as illustrated in FIGS. 1 and 4, while in the high profile state the fingers 43 are radially expanded as illustrated in FIGS. 2 and 5.

The fingers 43 diverge as they expand radially. This divergence tends to create a space (shown generally at 45 in FIG. 5a) between adjacent fingers 43, a space which increases toward the outermost diameter of the expanded fingers 43. While the expanded fingers in this state provide suitable means for anchoring the catheter 10, these spaces 45 prohibit any appreciable degree of occlusion.

In an embodiment where an occlusion function is desired as well as the anchoring function, an elastomeric sleeve 50 can be provided for disposition over the fingers 43. As the fingers 43 expand, the elastomeric sleeve 50 also expands providing a continuous surface 52 (best shown in FIG. 5) which faces distally of the catheter 10. In a preferred embodiment, this surface 52 is concave and extends increasingly radially with progressive proximal positions along the axis 17 of the catheter 10.

Although the outer surface 30 of the fingers 43 can be bonded or otherwise fixed to the inner surface of the sleeve 50, this is not the case in a preferred embodiment where the fingers 43 are free to slide on the inner surface of the sleeve 50.

If the central element, such as the tube 18, has the configuration of a rod, without the central lumen 25, then the sleeve 50 need only be sealed to the outer surface 30 at the proximal section 38 and the distal section 41. Alternatively, the sleeve 50 can fully enclose the distal end of the catheter 10. In the illustrated embodiment wherein the central element, such as the tube 18, has the central lumen 25, it may be desirable that the sleeve 50 also form a central lumen 54 at the distal end of the catheter 10. This will enable a user to dispense a fluid, such as an injectate, from the catheter 10 through the central lumen 25 of the tube 18, and the central lumen 54 of the sleeve 50 into the conduit 15.

In either case, the sleeve 50 can be disposed to cover the fingers 43 so that expansion of the fingers 43 will carry the sleeve 50 radially outwardly into engagement with the walls of the conduit 15. Then, when the fingers 43 are radially expanded, the sleeve 50 is also expanded and forms the continuous surface 52 which occludes or otherwise blocks the conduit 15. Thus the sleeve 50 provides means for closing the spaces 45 which develop as the fingers 43 diverge in their radial expansion.

The elastomeric characteristics of the sleeve 50 can be extended beyond the distal end of the tube 18 to form a nose or soft tip 56 at the distal end of the catheter 10. This soft tip 56 will reduce any trauma which may result from insertion of the catheter 10 into the conduit 15. In such an embodiment the central lumen 54 would extend through the tip 56.

Proximally of the tip section 16, various mechanisms can be used to move the distal section 41 relative to the proximal section 38 and thereby expand and collapse the fingers 43. This mechanism would also expand and collapse the elastomeric sleeve 50 in an embodiment wherein the sealing function was desired in addition to the anchoring function.

One such mechanism is illustrated in FIGS. 1 and 2, and includes a housing 61 disposed around an axis 63 which may be different than the axis 17. For example it may be desirable to form a bend 65 in the catheter 10 so that the axis 63 is disposed at an angle, such as 20°, to the axis 17 This bend 65 will tend to be fixed in the inner tube 18 which will have a higher degree of rigidity than the outer tube 27 in the embodiment of FIG. 1. Nevertheless, the bend 65 will also occur in the outer tube 27 in spite of the flexibility it will require to slide freely over the tube 18 and around the bend 65 to the proximal section 38.

Both the inner tube 18 and the outer tube 27 extend into the housing 61. In the illustrated embodiment the tube 18 projects proximally of the tube 27 and is bonded to a bushing 67 having a radial flange 70 which is received in a radial recess 72 formed by the housing 61. The bushing 67 retains the inner tube 18 in an axially fixed relationship with respect to the housing 61. An infusion tube 74 can be connected to either the tube 18 or the bushing 67 to accommodate the injection of an infusate, typically through a stopcock 76, into the central lumen 25 of the inner tube 18. In the illustrated embodiment, this infusate flows through the central lumen 25 and through the nose 56 of the sleeve 50 to exit the catheter 10 distally of the occlusive seal formed between the catheter 10 and the conduit 15.

Distally of the bushing 67 in the illustrated embodiment is a subassembly 81 which is fixed to the outer tube 27 but which is movable axially of the housing 61 and therefore the inner tube 18. This subassembly 81 includes a thumb tab 83 which is disposed exteriorly of the housing 61, and tube engagement portions 85 which are disposed interiorly of the housing 61. In a preferred embodiment, the subassembly 81 provides means disposed proximally of the tip section 16 for changing the fingers 43 and sleeve 50 between the low profile state and the high profile state.

The subassembly 81 is adapted to be slidably mounted to extend through a slot 90 in a wall 92 of the housing 61. This wall 92 is configured to extend between opposing flanges 94, 96 of the subassembly 81. In a preferred embodiment, the wall 92 is provided with transverse recesses or notches shown generally at 98, and the flange 96 is provided with at least one mating tooth 101 to form a ratchet or detent between the subassembly 81 and the housing 61.

It is the purpose of the tube engagement portions 85 to provide a fixed relationship with the outer tube 27 while facilitating a sliding or otherwise movable relationship with the inner tube 18. In the illustrated embodiment, these functions are achieved by a (FIG. 3) distal flange 105 and a proximal flange 107. The flange 107 extends transverse to the axis 63 and defines an axial slot 112 which provides a snap fit with the outer tube 27, but a sliding relationship with the inner tube 18.

The proximal flange 107 also extends transverse of the axis 63 in a generally parallel relationship with the flange 105. The flange 107 can also be provided with an axial slot 114 (FIG. 3a) in this case the slot 114 is sized to provide a snap fit with the inner tube 18.

It is important to this embodiment that the flanges 105 and 107 be fixed relative to the outer tube 27. This can be accomplished by gluing or otherwise bonding the outer surface 30 to the flange 107. Another way of accomplishing this objective is to provide a bushing 118 which is bonded to the outer tube 27 between the flanges 105, 107. This bushing 118 provides the outer tube 27 with an increased radius proximally of the flange 105 and distally of the flange 107. If the axial slot 112 in the flange 105 is sized to accommodate only the diameter of the tube 27, then the bushing 118 will inhibit any distal movement of the outer tube 27 relative to the thumb tab 83. Similarly, if the axial slot 114 in the flange 107 is appropriately sized to accommodate only the diameter of the inner tube 18, both the outer tube 27 and the bushing 118 will inhibit any proximal movement of the tube 27 relative to the thumb tab 83.

Although the catheter 10 can be adapted for occluding any orifice or body conduit, it is particularly useful in a procedure referred to as cholangiography. This procedure is one of several surgical operations which address the dramatic problems which can result from the formation and migration of gallstones emanating from the gall bladder.

Figure 6:
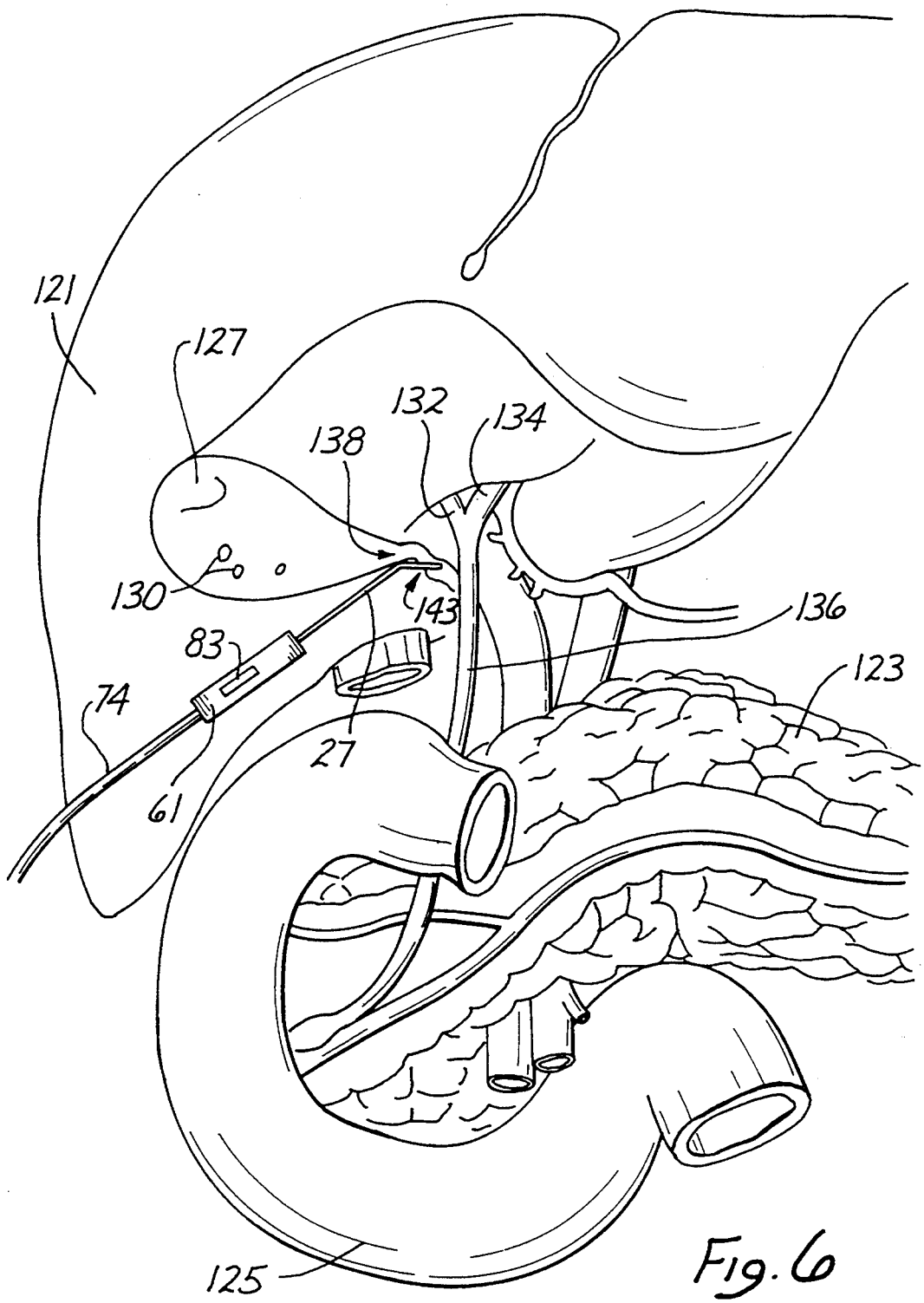
FIG. 6 is a perspective view of the abdominal organs including the liver and gall bladder, and illustrating a preferred method for using the catheter of the present invention.

Referring to FIG. 6 various body organs including a liver 121, pancreas 123, and duodenum 125, are illustrated relative to a gall bladder 127 which is the organ of origin for gallstones 130. One of the purposes associated with the pancreas 123 and the liver 121 is to create acids and other fluids which facilitate the digestion of food in the duodenum 125. By way of example, bile is created between the cells of the liver 121. This bile is collected in the branches of hepatic ducts 132,134, and conducted through a common bile duct 136 into the duodenum 125. At the junction of the common bile duct 136 and the duodenum 125, a sphincter muscle controls the flow of bile and pancreatic juices into the intestine. When these juices are not required for digestion, the valve closes causing the bile to back up in the common bile duct 136 and to flow into the gall bladder 127. It is the purpose of the gall bladder 127 to collect and concentrate this bile and to introduce it through a cystic duct 138 back into the common bile duct 136 when it is required for digestion.

One of the factors contributing to the formation of gallstones 130 is the general imbalance in this chemical, digestive system. These gallstones 130 tend to migrate into and ultimately occlude the cystic duct 138 and common bile duct 136. This has the dramatic effect of at least partially degrading the important digestive functions associated with the bile.

In at least one surgical procedure for addressing this problem, the gall bladder 127 is sacrificed in favor of inhibiting the formation of gallstones 130. This procedure, which ultimately requires removal of the gall bladder 127 has the attendant advantage of also removing any gallstones 130 which reside in the bladder 127. While this part of the procedure addresses the bladder 127 and the stone 130 contained therein, it is of course desirable to consider the possibility that there may be stones which have already migrated into the cystic duct 138 or the common bile duct 136.

Thus, this entire procedure, commonly referred to as a cholecystectomy, is begun by creating an incision 143 in the cystic duct 138 and introducing a cholangiography catheter, such as the catheter 10, through the incision 143 with the tip section 16 directed toward the common duct 136. With the catheter 10 having the capacity to achieve a low profile state, the incision 143 can be formed with only a minimal size.

When the sleeve 50 has been positioned in the cystic duct 138, the thumb tab 83 can be operated to move the proximal section 38 relative to the distal section 40. This will expand the fingers 43 and force the elastomeric sleeve 50 into both anchoring and sealing engagement with the interior surface of the duct 138. This procedure effectively occludes the duct 138 proximally of the nose 56 of the catheter 10.

An injectate, such as radiopaque dye, can then be injected through the stopcock 76, the inner tube 18, and the nose 56 to exit the catheter 10 into the cystic duct 138, the common bile duct 136, and the hepatic ducts 132. Appropriate visualization of this dye will highlight the location of any gallstones 130 in these ducts 132–138, and facilitate their removal in accordance with conventional procedures.

To complete the cholangiography procedure, the cystic duct 138 can be ligated or otherwise occluded, for example by application of a staple distally of the nose 56. The fingers 43 and sleeve 150 can then be collapsed to the low profile state and the catheter 10 removed through the incision 143. Ultimately, the gall bladder 130 is fully incised and removed from the body.

It can be seen from this particular use of the catheter 10 that both the anchoring and sealing functions associated with the fingers 43 and sleeve 50 are of particular importance to this invention. Both of these functions can be enhanced by reducing the area of contact between the sleeve 50 and the conduit 15. In a preferred embodiment, the seal has a circular configuration with a radial dimension greater than the normal inner diameter of the body conduit, but a longitudinal dimension less than this radial dimension. This provides a reduced area of contact between the sleeve 50 and the body conduit 15 so that the radial forces exerted by the fingers 43 can create an effective sealing pressure against the body conduit. In a preferred embodiment wherein the body conduit 15 may have an inner diameter such as 2 mm, the fingers 43 are expandable to a diameter such as 4 mm. As these fingers 43 contact the conduit 15, they form a circular seal which may have a dimension such as 1 mm measured along the axis 17.

It will be apparent that the subassembly 81 for operating the fingers 43 can be otherwise configured to provide for the relative movement between the inner tube 18 and the outer tube 27. As an alternative to the foregoing embodiment, the outer tube 27 can be held stationary while the engagement portions 85 of the subassembly 81 extend through in the outer tube 27 to engage the inner tube 18. In this embodiment, operation of the thumb tab 83 moves the inner tube 18 within the stationary outer tube 27. In such an embodiment, the outer tube 27 would hold the proximal portions 38 stationary while the movable inner tube 18 would move the distal portions 41 to collapse and expand the fingers 43.

While various elements of the catheter 10 can be manufactured from many different materials, the preferred embodiment requires an inner tube 18 which is relatively flexible. This tube 18 can be formed from a co-polyester manufactured by Eastman Plastics and marketed under the trademark KODAR PETG. The outer tube 27 can be formed from a rigid material such as stainless steel. The elastomeric sleeve 50 in this preferred embodiment is manufactured from a thermal set elastomer such as C-flex ® manufactured by Concept Polymers Inc. of Clearwater, Fla.

In a preferred embodiment, the inner tube has an outside diameter of about 0.035 inches and an inside diameter of about 0.023 inches. The overlying outer tube 27 has an inside diameter of about 0.037 inches. Its outer diameter extends to about 0.050 inches and provides a snug fit with the sleeve 50 which has an outer diameter of about 0.083 inches.

While the catheter 10 has been discussed with reference to preferred embodiments which are particularly useful in a cholangiography procedure, it will be apparent that this occlusion catheter can be otherwise embodied to facilitate insertion into, movement through, anchoring within and occlusion of a body orifice or conduit. Various mechanisms for operating the tip section 16 between a collapse and expanded state will also be apparent. All of these variations are deemed to be within the scope of this invention which should be determined not merely by reviewing the discussed and illustrated embodiments, but rather by considering the full extent of the following claims.

I claim:

1. An occlusion catheter sized and configured for insertion into a body conduit having a wall extending axially of the conduit, the catheter being operable to occlude the body conduit and comprising:
   a catheter body having a longitudinal axis and an outer surface extending between a proximal end and a distal end of the catheter body;
   occlusion and anchoring means disposed in proximity to the distal end of the catheter body and having a low profile state and a high profile state, the occlusion and anchoring means in the low profile state facilitating insertion of the catheter into the body conduit, and in the high profile state anchoring the catheter body within the conduit and facilitating occlusion of the body conduit by the catheter;
   a plurality of fingers included in the occlusion and anchoring means and expandable from the low profile state to the high profile state, the fingers in the high profile state including a concave surface extending increasingly radially outwardly with progressive proximal positions along the surface to an outer radius to reduce the area of contact between the occlusion and anchoring means and the conduit and thereby increase the pressure of the occlusion and anchoring means on the conduit; and
   an elastomeric sleeve included in the occlusion and anchoring means and disposed in circumferential relationship with the fingers, the sleeve being expandable radially outwardly by the fingers to sealingly engage the wall of the body conduit at the outer radius of the fingers when the occlusion and anchoring means is in the high profile state.

2. The catheter recited in claim 1 further comprising means disposed proximally of the occlusion means for changing the state of the occlusion means between the low profile state and the high profile state.

3. The catheter recited in claim 1 wherein the occlusion means includes:
   portions of the catheter body defining a plurality of slits disposed in juxtaposition to each other near the distal end of the catheter, the slits extending at least partially longitudinally of the catheter body; and
   means engaging the catheter body for expanding the body portions radially outwardly into circumferential proximity with the body conduit.

4. The catheter recited in claim 2 wherein:
   the catheter body defines a longitudinal channel; and
   the changing means communicates with the occlusion means through the longitudinal channel.

5. The catheter recited in claim 4 wherein the changing means includes:
   an elongate element disposed in the longitudinal channel and engaging the catheter body distally of the occlusion means;
   a housing receiving the catheter body and the element, one of the catheter body and the element being fixed to the housing, the other of the catheter body and the element being movable relative to the housing;
   a tab extending through the housing and engaging the other of the catheter body and the element, the tab being movable to slide the other of the catheter body and the element relative to the one of the catheter body and the element at least proximally of the facilitating means; whereby
   movement of the tab changes the facilitating means between the low profile state and the high profile state.

6. The catheter recited in claim 5 whereas the elongate element is a rod.

7. The catheter recited in claim 5 wherein the elongate element comprises a tube disposed in the longitudinal channel and having a lumen facilitating injection of an injectate into the body conduit distally of the occlusion means.

8. A method for injecting a fluid into a body conduit, including the steps of:
   providing a catheter having a longitudinal configuration and walls defining a lumen extending from a proximal end of the catheter to a distal end of the catheter, the catheter including an occlusion device disposed at the distal end of the catheter and being operable to expand from a low profile state to a high profile state, the occlusion device in the high profile state having at least one concave surface extending radially outwardly to a maximum radius;
   inserting into the body conduit the catheter and the occlusion device in its low profile state;
   operating the occlusion device to expand the occlusion device from the low profile state to the high profile state, the occlusion device in the high profile state contacting the body conduit radially outwardly of the catheter to form a seal at the maximum radius between the occlusion device and the conduit;
   injecting the fluid through the lumen of the catheter and into the body conduit distally of the seal; whereby
   the seal inhibits retrograde flow of the fluid.

9. The catheter recited in claim 1, wherein the continuous surface formed by the sleeve in its expanded state has a maximum at the outer radius, a first concave portion facing from the outer radius toward the proximal end of the catheter, and a second concave portion facing from the outer radius toward the distal end of the catheter.

10. The occlusion catheter recited in claim 1 further comprising means disposed at the proximal end of the catheter for releasibly locking the occlusion means in the high profile state.

11. The occlusion catheter recited in claim 1 wherein the sleeve is impregnated into the fingers of the occlusion means.

12. The occlusion catheter recited in claim 1 wherein the sleeve comprises a membrane disposed circumferentially outwardly of the fingers of the occlusion means.

13. An occlusion and anchoring device sized and configured for positioning in a body conduit having a particular diameter, the device being operable when so positioned to occlude the conduit, comprising:
   a tube having an elongate configuration and including a wall defining a longitudinal channel which extends between a first end of the tube and a second end of the tube;
   a plurality of fingers defining at least a pair of slots extending longitudinally between the first end of the tube and the second end of the tube;
   means for moving the first end of the tube between a first position wherein the fingers of the tube have a first diameter less than the particular diameter of the conduit and a second position wherein the fingers of the tube have a second diameter greater than the particular diameter of the conduit; and
   occlusion and anchoring means carried by the fingers for forming at least one concave surface extending outwardly to a maximum radius to reduce the area of contact between the occlusion and anchoring means and the conduit and thereby increase the pressure of the occlusion and anchoring means on the conduit and for creating a circumferential seal with the conduit at the maximum radius when the first end of the tube is in the second position.

14. The occlusion device recited in claim 13 wherein the moving means includes:
   a central element disposed in the longitudinal channel of the tube and having a slidable relationship with the first end of the tube and a fixed relationship with the second end of the tube; and
   means engaging one of the central element and the tube for sliding the central element relative to the tube to expand the fingers of the tube to the second diameter and to collapse the fingers of the tube to the first diameter.

15. The occlusion device recited in claim 14 wherein the central element has a tubular configuration and a central lumen which extends between the first end of the tube and the second end of the tube.

16. The occlusion device recited in claim 13 wherein operation of the moving means from the first position to the second position draws the second end of the tube into proximity with the first end of the tube and expands the fingers of the tube radially outwardly.

17. An infusion device for injecting an infusate into a body conduit, comprising:
   a catheter having a first tube with a lumen extending between a proximal end and a distal end of the first tube, and a second tube slidably disposed in the lumen of the first tube and having an exit port at a distal end of the second tube;
   an elastomeric sleeve disposed proximally of the exit port and having a first end of the sleeve attached to the distal end of the first tube and a second end of the sleeve attached to the distal end of the second tube;
   means disposed along the sleeve and operable for expanding the sleeve radially outwardly to a particular configuration having a concave shape and a maximum radius;
   means disposed at the proximal end of the first tube for operating the expanding means to form a seal with the conduit at the maximum radius of the expanding means; and
   means for injecting the infusate through the second tube and the exit port into the body conduit distally of the seal.

18. The infusion device recited in claim 17 wherein the seal has the configuration of a circle generally concentric with the axis of the catheter.

19. The infusion device recited in claim 18 wherein the circular seal has the configuration of a cylinder having an axial dimension and a radial dimension, the axial dimension of the cylinder being less than the radial dimension of the cylinder.

20. The infusion device recited in claim 17 further comprising detent means disposed at the proximal end of the first tube for releasably locking the expanding means in the particular configuration.

21. The infusion device recited in claim 17 wherein the body conduit has a first axis, the catheter has a second axis, and the first axis is generally parallel to the second axis when the anchoring means is in the high profile state.

22. An infusion device for injecting an infusate into a body conduit, including:
   a catheter body having an infusion lumen extending between a proximal end and a distal end of the catheter;
   means for injecting the infusate through the lumen of the catheter body and into the conduit, the injection of the infusate creating a force which tends to move the catheter body axially within the conduit;
   means disposed at the distal end of the catheter for anchoring the catheter body within the conduit to oppose the axial movement of the catheter body within the conduit, the anchoring means having a low profile state and being operable to expand to a high profile state; and
   the anchoring means in the high profile state including a concave surface extending increasingly radially outwardly with progressive proximal positions along the surface to reduce the area of contact between the anchoring means and the conduit and thereby increase the pressure of the anchoring means on the conduit; whereby
   the increased pressure enhances the anchoring characteristics of the catheter to oppose migration of the catheter body during infusion of the infusate.

23. The infusion device in claim 22 wherein:
   the anchoring means includes a plurality of fingers separated by spaces which have a first radial dimension in the low profile state and a second radial dimension greater than the first radial dimension in the high profile state; and
   the catheter further comprises means for connecting the fingers of the anchoring means to close the spaces between the fingers and produce an occlusion barrier between the conduit and the catheter body.

24. The infusion device recited in claim 23 wherein the connecting means comprises a sleeve disposed circumferentially outwardly of the fingers.

25. A catheter sized and configured for insertion into a body conduit having a range of diameters, the catheter comprising:
   a catheter body having a longitudinal axis extending between a proximal end and a distal end, the catheter body having a diameter less than the range of diameters to facilitate axial movement of the catheter body to and from an operative site within the body conduit;
   means for anchoring the distal end of the catheter body at the operative site in the body conduit, the anchoring means having a low profile state facilitating insertion of the catheter into the body conduit, and a high profile state facilitating anchoring of the catheter in the body conduit at the operative site;
   the anchoring means in the high profile state having a plurality of shapes each including a concave surface facing distally from extending radially outwardly of the catheter body with progressive proximal positions to a maximum diameter which is variable within the range of diameters of the conduit;
   means disposed at the proximal end of the catheter body for moving the anchoring means between the low profile state and the high profile state; and
   a plurality of detents included in the moving means for releasably locking the anchoring means at an associated one of the plurality of shapes with the maximum diameter of the anchoring means disposed in circumferential sealing relationship with the conduit to anchor the catheter at the operative site in the conduit.

26. A cholangiography catheter sized and configured for insertion into a body conduit and operable to occlude the body conduit, the catheter comprising:
   a catheter body having an outer surface extending along a proximal portion and a distal portion of the catheter body;
   a first axis extending through the proximal portion of the catheter body;
   a second axis having at least a component transverse to the first axis and extending through the distal portion of the catheter body;
   occlusion means disposed in proximity to the distal end of the catheter body and having a low profile state and a high profile state, the occlusion means in the low profile state facilitating insertion of the catheter into the body conduit, and in the high profile state facilitating occlusion of the body conduit by the catheter;
   a plurality of fingers included in the occlusion means and expandable from the low profile state to the high profile state, the fingers in the high profile state having a concave configuration and extending to an outer radius; and
   an elastomeric sleeve included in the occlusion means and disposed in circumferential relationship with the fingers, the sleeve being expandable radially outwardly by the fingers to sealingly engage the body conduit at the outer radius of the fingers when the occlusion means is in the high profile state.

27. An occlusion device adapted for insertion into a body conduit and operable to occlude the body conduit, the device comprising:
   a catheter having a first tube with a lumen extending between a proximal end and a distal end of the first tube, and a second tube slidably disposed in the lumen of the first tube;
   an elastomeric sleeve disposed between the first tube and the second tube, the sleeve having a first end attached to the distal end of the first tube and a second end attached to the distal end of the second tube;
   means disposed along the sleeve and operable for expanding the sleeve radially outwardly to a particular configuration having a concave shape and a maximum radius; and
   means disposed at the proximal end of the first tube for operating the expanding means to form a circumferential seal with the conduit at the maximum radius of the expanding means.

28. An occlusion device adapted for insertion into a body conduit and operable to occlude the body conduit, including;
   a catheter body having a lumen extending between a proximal end and a distal end of the catheter body;
   means disposed at the distal end of the catheter body for anchoring the catheter body within the conduit to oppose axial movement of the catheter body within the conduit, the anchoring means having a low profile state and being operable to expand to a high profile state to occlude the body conduit; and
   the anchoring means in the high profile state including a concave surface extending increasingly radially outwardly with progressive proximal positions along the surface, to reduce the area of contact between the anchoring means and the conduit and thereby increase the pressure of the anchoring means on the conduit.

29. The occlusion device recited in claim 13 wherein the occluding means includes a sleeve disposed in circumferential relationship with the tube, the sleeve having elastomeric properties for expanding radially outwardly with movement of the fingers from the first position to the second position.

* * * * *